(12) United States Patent
Wilson et al.

(10) Patent No.: US 9,050,436 B2
(45) Date of Patent: Jun. 9, 2015

(54) ADJUSTABLE RESISTANCE, GRAVITATIONALLY ACTIVATED, ANTI-SYPHON VALVE

(71) Applicant: DePuy Synthes Products, LLC, Raynham, MA (US)

(72) Inventors: Stephen Wilson, North Easton, MA (US); Alyssa Trigger, South Boston, MA (US)

(73) Assignee: DePuy Synthes Products, LLC, Raynham, MA (US)

( * ) Notice: Subject to any disclaimer, the term of this patent is extended or adjusted under 35 U.S.C. 154(b) by 102 days.

(21) Appl. No.: 13/803,905

(22) Filed: Mar. 14, 2013

(65) Prior Publication Data

US 2014/0276349 A1  Sep. 18, 2014

(51) Int. Cl.
*A61M 27/00* (2006.01)
*A61M 25/00* (2006.01)

(52) U.S. Cl.
CPC ......... *A61M 27/006* (2013.01); *A61M 25/0009* (2013.01)

(58) Field of Classification Search
CPC .......................................... A61M 27/00–27/006
USPC ....................................................... 604/8–10
See application file for complete search history.

(56) References Cited

U.S. PATENT DOCUMENTS

| 1,806,356 A | 5/1931 | Lynn et al. |
|---|---|---|
| 3,320,971 A | 5/1967 | Hemenway |
| 3,758,073 A | 9/1973 | Schulte |
| 4,023,591 A | 5/1977 | Short et al. |
| 4,030,520 A | 6/1977 | Sands |
| 4,114,603 A | 9/1978 | Wilkinson |
| 4,187,874 A | 2/1980 | Essebaggers |
| 4,332,255 A | 6/1982 | Hakim et al. |
| 4,443,214 A | 4/1984 | Marion |
| 4,475,899 A | 10/1984 | Muller |
| 4,540,400 A | 9/1985 | Hooven |
| 4,551,128 A | 11/1985 | Hakim et al. |
| 4,553,956 A | 11/1985 | Muller |
| 4,605,395 A | 8/1986 | Rose et al. |
| 4,633,681 A | 1/1987 | Webber |
| 4,673,384 A | 6/1987 | Marion |
| 4,675,003 A | 6/1987 | Hooven |
| 4,676,772 A | 6/1987 | Hooven |
| 4,681,559 A | 7/1987 | Hooven |
| 4,714,458 A | 12/1987 | Hooven |

(Continued)

FOREIGN PATENT DOCUMENTS

| DE | 195 35 637 A1 | 3/1997 |
|---|---|---|
| EP | 2 253 352 A1 | 11/2010 |

*Primary Examiner* — Philip R Wiest
*Assistant Examiner* — Benjamin Klein
(74) *Attorney, Agent, or Firm* — Troutman Sanders LLP

(57) ABSTRACT

An anti-siphon drainage device having a housing forming an internal chamber, an inlet and outlet ports part of the internal chamber and fluidly connected by a primary flow path. A valve seat is associated with the primary flow path, a sloped section extends from the valve seat, and a valve element disposed in the sloped section and can seat in the valve seat to restrict a fluid flow into the primary flow path from the inlet port. A secondary flow path can have an opening near the inlet port and an orifice near the outlet port. A regulator has an aperture to selectively open and close the opening of the secondary flow path. When the valve element is seated in the valve seat and restricting the fluid flow into the primary flow path, the fluid flows into the secondary flow path.

20 Claims, 8 Drawing Sheets

(56) References Cited

U.S. PATENT DOCUMENTS

| | | |
|---|---|---|
| 4,714,459 A | 12/1987 | Hooven |
| 4,729,762 A | 3/1988 | Doumenis |
| 4,769,002 A | 9/1988 | Hooven |
| 4,776,838 A | 10/1988 | Sainte-Rose et al. |
| 4,776,839 A | 10/1988 | Doumenis |
| 4,781,672 A | 11/1988 | Hooven |
| 4,787,419 A | 11/1988 | Megee et al. |
| 4,795,437 A | 1/1989 | Schulte et al. |
| 4,861,331 A | 8/1989 | East et al. |
| 4,867,740 A | 9/1989 | East |
| 4,875,059 A | 10/1989 | Masuda |
| 4,883,456 A | 11/1989 | Holter |
| 5,042,974 A | 8/1991 | Agarwal |
| 5,336,166 A | 8/1994 | Sierra |
| 5,368,556 A | 11/1994 | Lecuyer |
| 5,437,627 A | 8/1995 | Lecuyer |
| 5,643,195 A | 7/1997 | Drevet et al. |
| 5,928,182 A | 7/1999 | Kraus et al. |
| 6,126,628 A * | 10/2000 | Nissels ........................ 604/9 |
| 6,280,176 B1 | 8/2001 | Boyce et al. |
| 6,802,331 B2 | 10/2004 | Arnold et al. |
| 6,905,474 B2 | 6/2005 | Borgesen |
| 6,926,246 B2 | 8/2005 | Ginggen |
| 6,926,691 B2 | 8/2005 | Miethke |
| 7,931,612 B2 | 4/2011 | Rosenblatt |
| 8,177,737 B2 | 5/2012 | Negre et al. |
| 2006/0089589 A1 | 4/2006 | Portnoy |
| 2007/0093741 A1 | 4/2007 | Miethke |
| 2010/0056980 A1 | 3/2010 | Negre et al. |
| 2010/0217232 A1 | 8/2010 | Rosenblatt |
| 2010/0307758 A1 | 12/2010 | Vick, Jr. et al. |

\* cited by examiner

FIG. 8

| Settings | Resistance | Description | Fixed Port | F1 | F2 | F3 |
|---|---|---|---|---|---|---|
| 1 | Closed | No FPs open | Move 4 units | | | |
| 2 | R1 | F1 only open | Move 4 units | | | |
| 3 | R2 | F2 only open | Move 4 units | | | |
| 4 | R3 | F1 and F2 open | Move 4 units | | | |
| 5 | R4 | F3 only open | Move 4 units | | | |
| 6 | R5 | F1 and F3 open | Move 4 units | | | |
| 7 | R6 | F2 and F3 open | Move 4 units | | | |
| 8 | R7 | All FPs open | Move 4 units | | | |

ADJUSTABLE RESISTANCE, GRAVITATIONALLY ACTIVATED, ANTI-SYPHON VALVE

FIELD OF THE INVENTION

The present invention relates to a valve system for treating hydrocephalus.

BACKGROUND

Shunt systems for directing body fluid from one region to another are known in the medical field. One application for such a fluid shunt system is in the treatment of hydrocephalus in order to direct cerebrospinal fluid ("CSF") away from the brain and into the venous system or to another region of the body. In this application, a shunt is implanted on the patient's skull, under the scalp, and is coupled to a brain ventricle catheter which is adapted for insertion into the brain and to a distal catheter which is adapted for insertion into the drainage region, such as the peritoneal cavity, the atrium or other drainage site.

The shunt systems typically include a pressure-regulated valve to control the flow rate of the CSF. The distal catheter is typically implanted caudal to the ventricular inlet which causes the shunt system to act as a siphon when the patent is in the upright position. The siphoning effect can cause overdrainage that can lead to low pressure headaches, slit ventricles, and subarachnoid hemorrhages.

Anti-siphoning has previously been addressed with several mechanisms, including weighted ball and seat valves, flow control valves, and diaphragm valves. In turn, the weighted ball and seat valves contain one or more balls or other mechanism, that when acted on by gravity, i.e. when the patient is upright, the ball seats in the valve passage and closes the fluid pathway. Closing a primary fluid pathway can lead to underdrainage if the alternate pathway does not provide sufficient drainage as well. Another ball and seat design closes in response to excessive flow, but offers a secondary pathway that always remains open, allowing for constant drainage, but the resistance of the secondary pathway remains fixed. Diaphragm valves are typically in the closed flow position and only opening in response to positive pressure and closing again when under negative distal pressure. A diaphragm valve has its disadvantages, in that it can become encapsulated by tissue and fails to open under positive pressure, this leads to underdrainage.

Examples of previous solutions include U.S. Pat. No. 4,605,395 to Rose et al. disclosing a single flow path ball and seat valve and U.S. Pat. No. 4,681,559 to Hooven, having two flow paths, but both have pressure valves. U.S. Pat. No. 6,126,628 Nissels is a pressure valve with a tortuous secondary flow path. However, the secondary flow path has fixed flow characteristics. Additionally, U.S. Pat. No. 8,177,737 to Negre et al. is a pressure valve with numerous secondary ports, but the flow to certain ports is controlled by the location of the ball in the primary flow path. Thus, the need exists for an anti-siphon valve of simple design, yet having multiple flow and pressure characteristics.

SUMMARY

Accordingly, the present invention provides tools and methods for simply controlling the siphoning effect caused by the implantation of certain shunt-systems. The examples of the present invention provide gravitationally assisted anti-siphoning valves wherein control over the siphoning rate is directly related to the number of open fluid passageways. Each secondary pathway can provide equal fluid flow resistance, such that each setting of the device is a multiple of the resistance of the single pathway. Alternately, each pathway can have its own unique resistance profile and flow is controlled by selecting the appropriate pathway. In one example, the user can select one or more pathway configurations to control the flow, without complex mechanisms that can potentially be obscured by tissue.

An anti-siphon drainage device can have a housing forming an internal chamber, inlet and outlet ports can be part of the internal chamber and fluidly connected by a primary flow path. A valve seat is associated with the primary flow path, a sloped section extends from the valve seat, and a valve element is disposed in the sloped section and can seat in the valve seat to restrict a fluid flow into the primary flow path from the inlet port. A secondary flow path can have an opening near the inlet port and an orifice near the outlet port. A regulator has an aperture to selectively open and close the opening of the secondary flow path. When the valve element is seated in the valve seat and restricting the fluid flow into the primary flow path, the fluid flows into the secondary flow path.

The anti-siphon drainage device can have the inlet port disposed approximately above the outlet port in a vertical direction, causing the valve element to enter the valve seat and restrict the fluid flow to the primary flow path. Contrary, when the inlet port is disposed approximately parallel the outlet port in a horizontal direction, the valve seat allows the fluid flow into the primary flow path. One of the valve element or the valve seat can allow a restricted fluid flow into the primary flow path when seated (i.e. a "leaky valve"). The disposition of the valve element in the valve seat can be controlled by gravity.

The primary flow path can be hydraulically larger than the secondary flow path. Some examples have the secondary flow path spiraled around the primary flow path. In others, they can be any shape or straight.

Another example of the anti-siphon drainage device can have a second secondary flow path separate from the secondary flow path having a second opening. The secondary flow path and the second secondary flow path can spiral around the primary flow path as a double threaded screw. The regulator can include a plurality of second apertures, which along with the aperture, are configured to selectively open and close the opening and the second opening.

A yet further example can also have a third secondary flow path separate from both the secondary flow path and the second secondary flow path, and having a third opening. The regulator now has a plurality of second apertures, which along with the aperture, are configured to selectively open and close the opening, the second opening, and the third opening. The regulator can have different settings to selectively open and close the opening, the second opening, and the third opening. The settings can have at least one of the following configurations: all open, all closed, each of the openings individually opened, and pairs of openings opened.

Furthermore, an example can have the primary flow path having a primary hydraulic capacity (P1), the secondary flow path having a secondary hydraulic capacity (F1), the second secondary flow path having a third hydraulic capacity (F2), and the third secondary flow path having a fourth hydraulic capacity (F3). The hydraulic relationship between them can be: F1<F2<F3<P1. Alternately, the hydraulic relationship can be: F1<F2<F1+F2<F3<F1+F3<F2<F3<F1+F2+F3<P1.

A method of forming an anti-siphon drainage device like that described above can include the steps of forming the primary flow path with the valve seat; disposing the valve element in the sloped section; forming the secondary flow path; and disposing the regulator over the secondary flow path to selectively occlude the secondary flow path. Forming the secondary flow path can include spiraling the secondary flow path around the primary flow path. The primary flow path can be formed with a first hydraulic characteristic, and the secondary flow path can be formed with a second hydraulic characteristic. In an example, the first hydraulic characteristic is greater than the second hydraulic characteristic.

BRIEF DESCRIPTION OF THE DRAWINGS

This invention is described with particularity in the appended claims. The above and further aspects of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

The drawing figures depict one or more implementations in accord with the present teachings, by way of example only, not by way of limitation. In the figures, like reference numerals refer to the same or similar elements.

FIG. 8 is a table illustrating the apertures, secondary flow paths, and the flow resistance level.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

Figure 1:
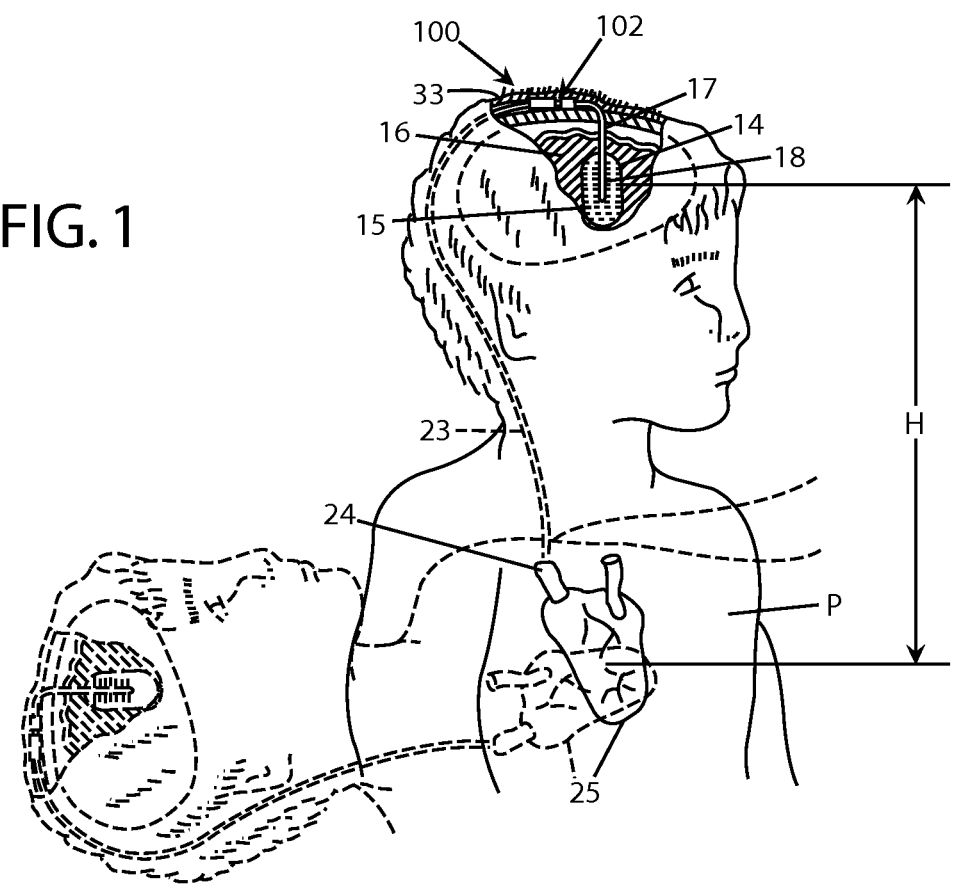
FIG. 1 illustrates an example of the placement of an anti-siphon device of the invention relative to a fluid shunt system disposed in a patient.
Figure 2:
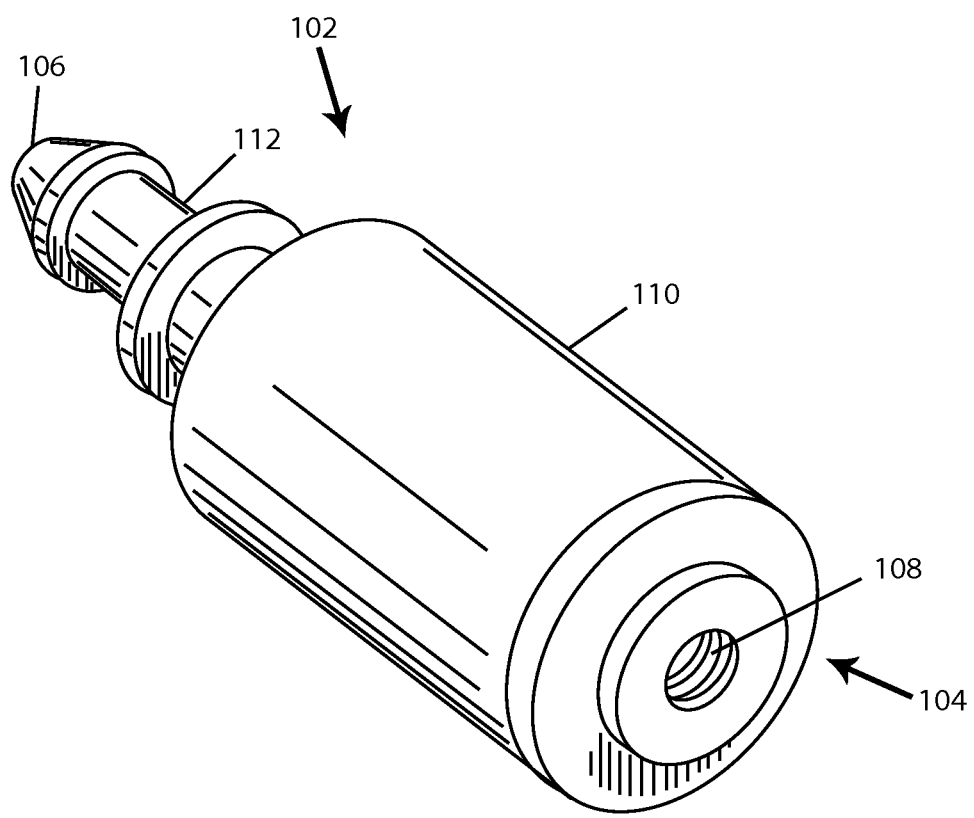
FIG. 2 is an isometric view of an example of anti-siphon device in accordance with the invention.

Referring to the drawings, and particularly to FIGS. 1 and 2, a CSF anti-siphon pressure relief valve system 100 for maintaining a desired predetermined intracranial pressure in a patient P is illustrated. The system 100 includes an adjustable resistance, gravitationally activated, anti-siphon device 102 constructed in accordance with the present invention for maintaining a desired intracranial pressure.

Cerebrospinal fluid (CSF) 14 is drained from a ventricle 15 of the brain 16 by means of a ventricular catheter 17. Preferably, the catheter is radio-opaque in order to facilitate its accurate placement within the brain. The distal end 18 of the catheter allows the passage of CSF therethrough and is positioned in a suitable brain ventricle. The other end of the catheter is coupled to an inlet port 104 of the anti-siphon device 102 to establish fluid communication between the system 100 and the ventricle. The outlet port 106 of the valve system is attached to one end of a drain catheter 23, the opposite end of which discharges into an appropriate location in the patient's body. Although the drain catheter is shown threaded through an appropriate vein 24 to terminate within the right atrium of the heart 25, a different drainage location, such as, for example, the peritoneal cavity, could be selected instead. When open, the system 100 allows passage of CSF from the brain ventricle to the selected discharge location to relieve excessive intracranial pressure caused by excessive accumulation of CSF.

While an increased differential pressure may result from the excessive accumulation of CSF in the brain ventricle, such an increase might also be a perfectly normal response to ordinary physical activity of the patient. For example, when a patient stands after lying for some time in a recumbent position, as illustrated in phantom in FIG. 1, the differential pressure will suddenly increase by reason of the sudden increase in vertical height H in the fluid column existing between the distal end of the ventricular catheter 17 and the drainage location. If a relief valve of the system were to open and permit unrestrained fluid flow in response to this pressure increase, overdrainage of the ventricle and a brain hematoma, are possible results. Further, the dimensions of the various parts described are selected so as to be compatible with subcutaneous implantation of the valve over the cranium 33.

Figure 3:
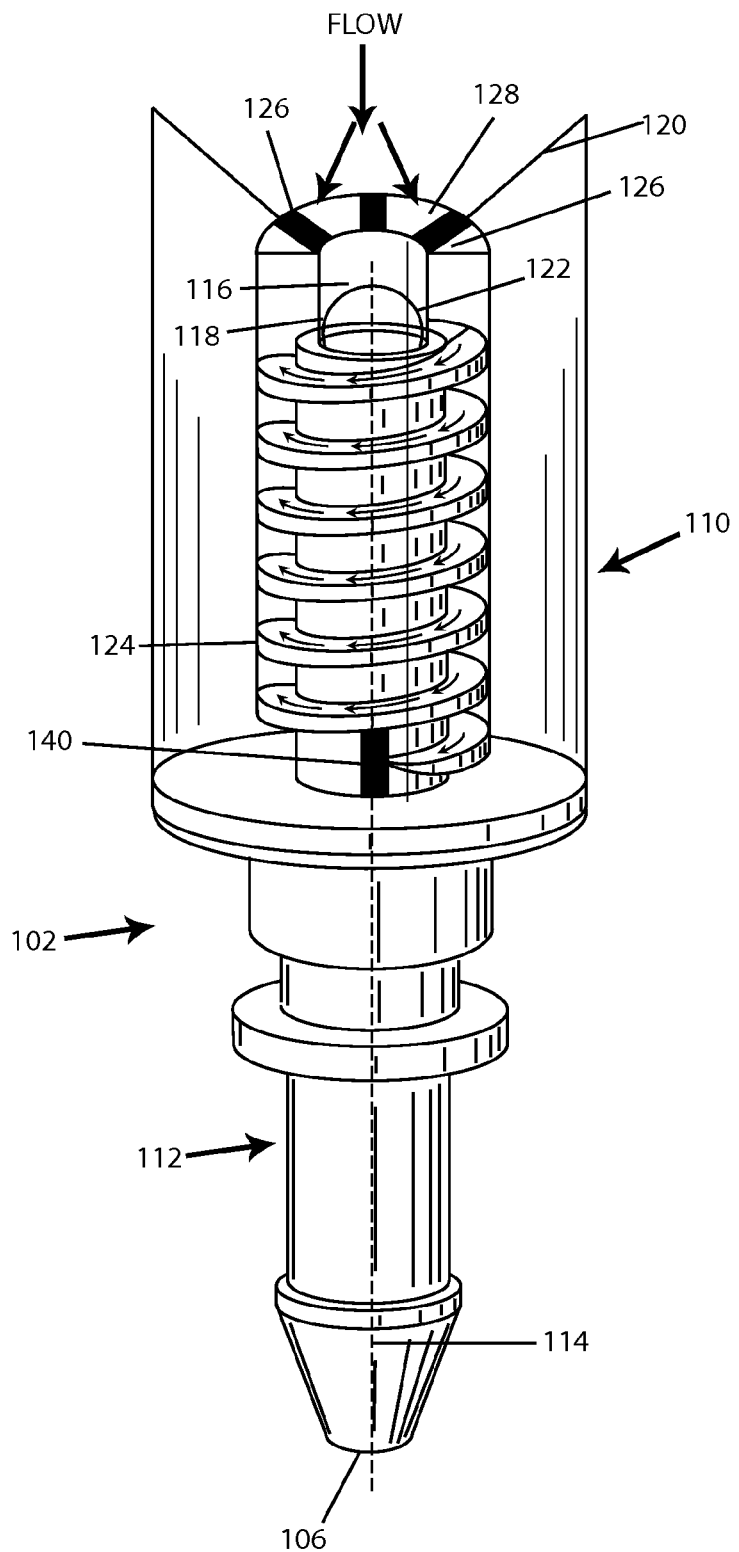
FIG. 3 is a front view of the anti-siphon device without the housing in the secondary flow position.
Figure 4:
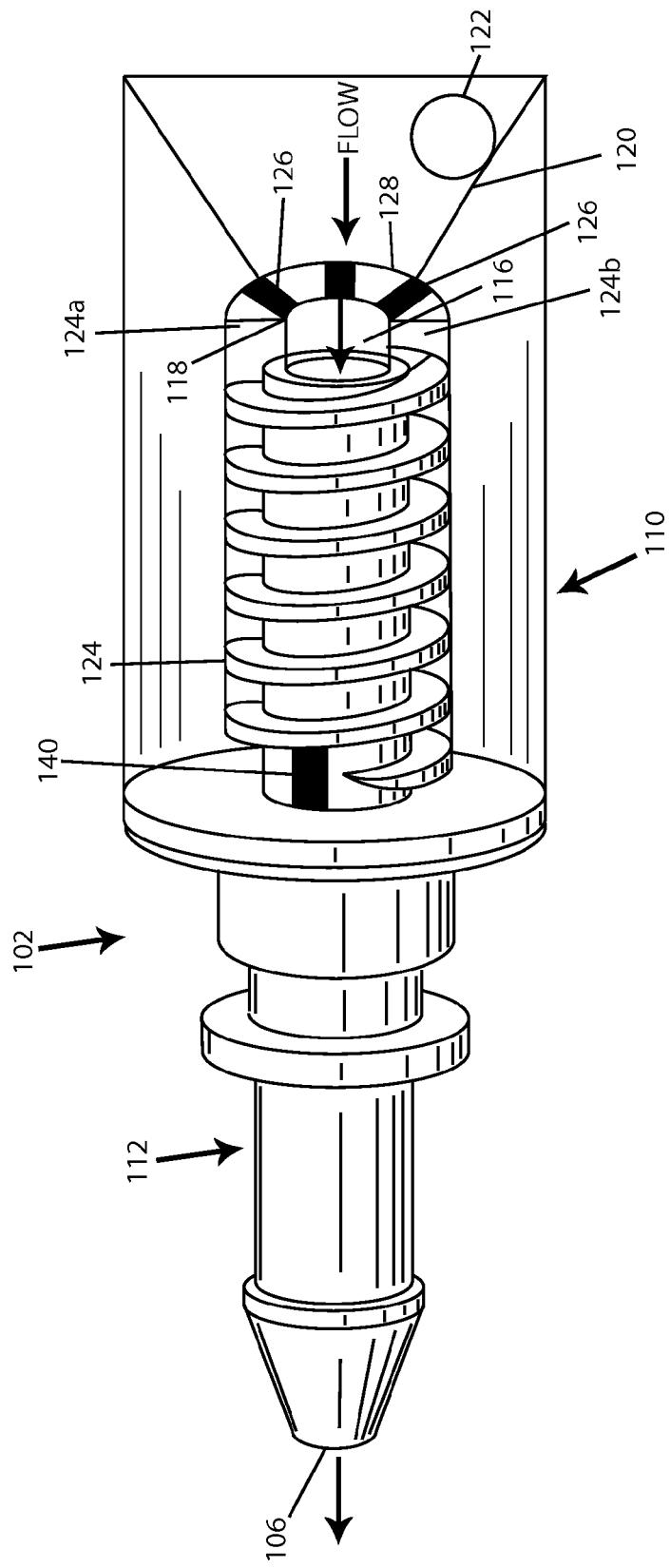
FIG. 4 is a front view of the anti-siphon device without the housing in the primary flow position.

Referring to FIGS. 2, 3 and 4, an example of the adjustable resistance, gravitationally activated, anti-siphon device 102 according to the invention is shown. The device 102 includes an inlet 104 in the form of an aperture 108 disposed in a housing 110 and an outlet 106 in the form of a connector 112 suitable for coupling to a drainage catheter 23. The housing 110 defines the inlet 104 at the proximal end of the device. The outlet 106 is at the distal end of the device 102 through which the fluid is directed from the device 102. The components of the device 102, including the housing 110, are fabricated with any suitable biocompatible material. Examples of such preferred materials include polyethersulfone (PES), polysulfone (PS), polyurethane, polyethylene and polypropylene.

FIGS. 3 and 4 illustrate a partial section through the housing 110. Through a midline 114 of the housing 110 is a primary flow path 116. The primary flow path 116 connects the inlet port 104 to the outlet port 106 and is the main fluid path for the CSF. At a point in the primary flow path 116 a valve seat 118 is disposed in and stems from one end of the primary flow path 116 approximate to the inlet port 104. Leading to the valve seat 118 is a sloped section 120. The sloped section 120 can angle from the inlet port 104 to the valve seat 118, where the narrowest section is at the valve seat 118. Disposed within the sloped section is valve element 122, which in one example can be a ball. Suitable materials for fabricating the ball 122 and seat 118 include synthetic ruby (aluminum oxide).

The valve element 118, in one example, is not pressure sensitive. For example, the valve element 118 is not biased using a resilient element (e.g. a spring) to be unseated only when the pressure at the outlet 106 reaches a predefined threshold. In this example, the valve element 118 is displaced by gravity dictated by the orientation of the valve 102.

When the housing 110 is in the upright position (i.e. the inlet port 104 is vertically higher than the outlet port 106) the ball 122 can be disposed in the seat 118 and the primary flow path 116 is sealed off by the ball 122 (see FIG. 3). In one example, the primary flow path 116 is completely sealed to fluid flow. In other examples, the seal maybe "leaky" and deliberately allow a small amount of fluid to pass into the primary flow path 116 even though the ball 122 is seated properly.

The sloped section 120 can direct the ball 122 into the valve seat 118 when the housing 110 is in the vertical position. In examples, the sloped section 120 can be conical or frusto-conical. In contrast, FIG. 4 illustrates the device 102 is the horizontal position, and the ball 122, by force of gravity, rolls down the sloped section 120 and out of the valve seat 118. This clears the primary flow path 116 and allows fluid to flow freely. The horizontal and vertical positions of the device typically correspond to a horizontal or vertical position of the patient (i.e. laying down or sitting up).

The device 102 can also include one or more secondary flow paths 124. The secondary flow paths 124 can transport fluid from the inlet 104 to the outlet 106 but are separate and distinct from the primary flow path 116 and in other examples are separate and distinct from each other. As an example, FIGS. 3 and 4 illustrate two secondary flow paths 124a, 124b as a spiral path formed from a double threaded screw. However, the secondary flow paths 124 can take any form and any number. The opening 126 for the secondary flow paths can be within the sloped section 120 but outside the valve seat 118. In one example, the ball 122 cannot seat in, and thus block, the secondary flow paths 124. The secondary flow paths 124 can then discharge to the outlet port 106 through an orifice 140.

Under primary flow conditions, as illustrated in FIG. 4, the primary flow channel 116 is open, because the ball 122 has rolled out, and the CSF preferentially flows through the primary flow path 116. This is when the patent is typically prone. FIG. 3 illustrates the secondary flow conditions when the patent is upright and gravity has placed the ball 122 into the seat 118, sealing off the primary flow path 116. In this condition, the fluid now must flow into the openings 126 of the secondary flow paths 124 to reach the outlet 106. Sealing the primary flow channel 116 prevents siphoning, while having secondary flow paths 124 continues to allow for drainage.

In an example, each of the primary and secondary flow paths can have the same, similar or different hydraulic characteristics, for example, at least flow rates. The primary flow path 116 can be hydraulically larger than the secondary flow paths 124. "Hydraulically larger" means that the primary flow path 116 can pass more fluid (i.e. a larger flow rate) than the secondary flow paths 124, but this can be for various reasons. One reason can be that the primary flow path 116 has a larger diameter (flow rate=velocity×area) or has a smaller hydraulic resistance (also a factor of velocity and path geometry, along with other elements). A smaller hydraulic resistance allows the fluid to flow easier. Additionally, it can be a combination of these and other elements that allow a higher flow rate through the primary flow path 116.

Figure 5A:
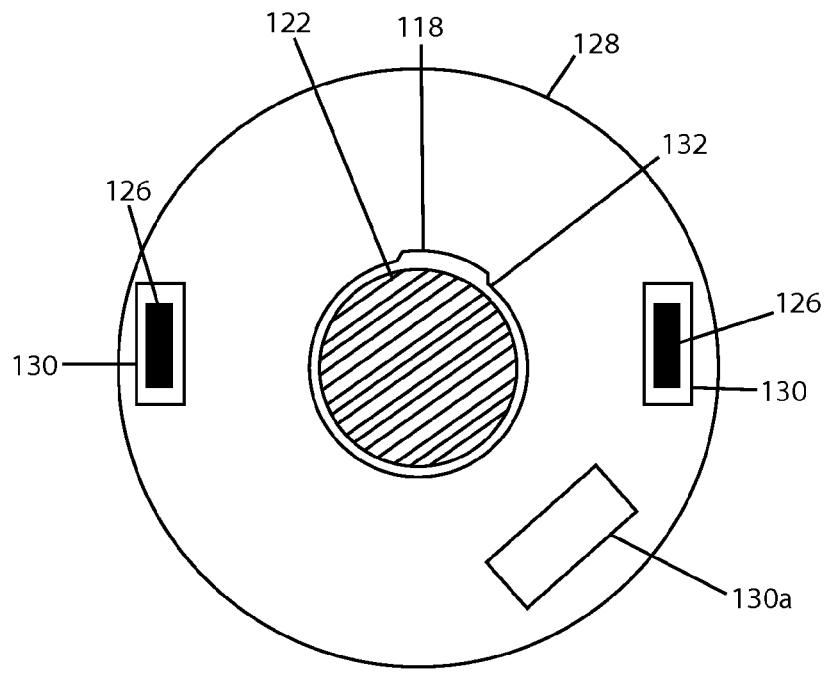
FIGS. 5A and 5B are a top section view of the anti-siphon device illustrating an example of a regulator.
Figure 5B:
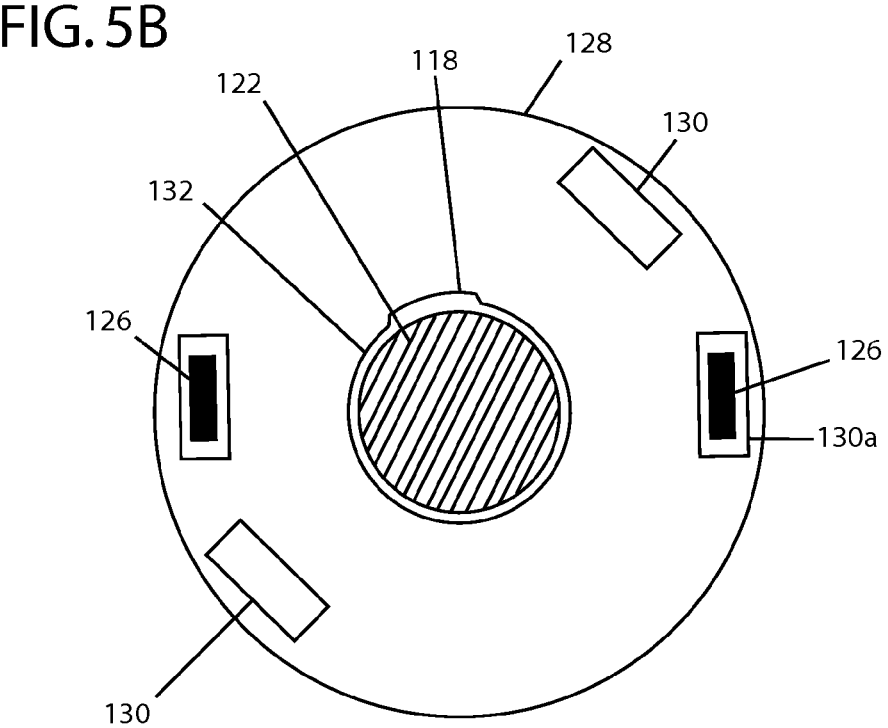

While, in certain examples, the ball 122 cannot block the secondary flow paths 124, the secondary flow paths 124 can still be regulated. FIGS. 5A and 5B illustrate a secondary flow path regulator 128. The regulator 128 can control the flow of fluid into the secondary flow paths 124 by partially or fully blocking the openings 126. In this example, the regulator 128 has three apertures 130. Two of the apertures 130 are illustrated in FIG. 5A as covering over both of the openings 126. This is the maximum secondary flow condition. Also illustrated is a third aperture 130a offset from the other two apertures 130. The regulator 128 can be rotated such that the third aperture 130a is over an opening 126. It can seen in FIG. 5B, that when the third aperture 130a is over one opening 126, for flow path 124a, the other opening 126, and thus flow path 124b, is occluded. One or either flow path 124a, 124b can be selected by rotation of the regulator 128. Further, in certain examples, there can be partial occlusion.

Additionally, the regulator 128 can have a valve element opening 132, allowing the valve element 122 unrestricted access to the valve seat 118. In an example, the regulator 128 cannot affect or block flow to the primary flow path 116. The purpose of the regulator 128, in one example, is only to regulate the flow to the secondary flow paths 124.

In certain examples, the regulator 128 is set by the surgeon prior to implanting the valve 102 into the patient. Particular rotations of the regulator 128 can result in differing secondary flow path rates and thus affect the intracranial pressure. Some valves can only be set by manual manipulation, which can require exposing the valve if the settings need to be changed once inside the patient. Other examples of the valve can have their settings changed without surgery.

Preventing flow into the primary flow path 116 when the valve 102 is upright prevents the siphoning effect. However, CSF still needs to be drained to prevent underdrainage. The secondary flow path 124 allows for continued drainage without a siphon effect. When the primary flow path 116 is opened (i.e. the valve element 122 is not seated in the valve seat 118) all or most of the fluid enters the primary flow path 116. While the secondary flow path 124 is still open, the hydraulic characteristics of the primary flow path 116 are such that the fluid preferentially takes the primary path, as the path of least resistance.

Figure 6:
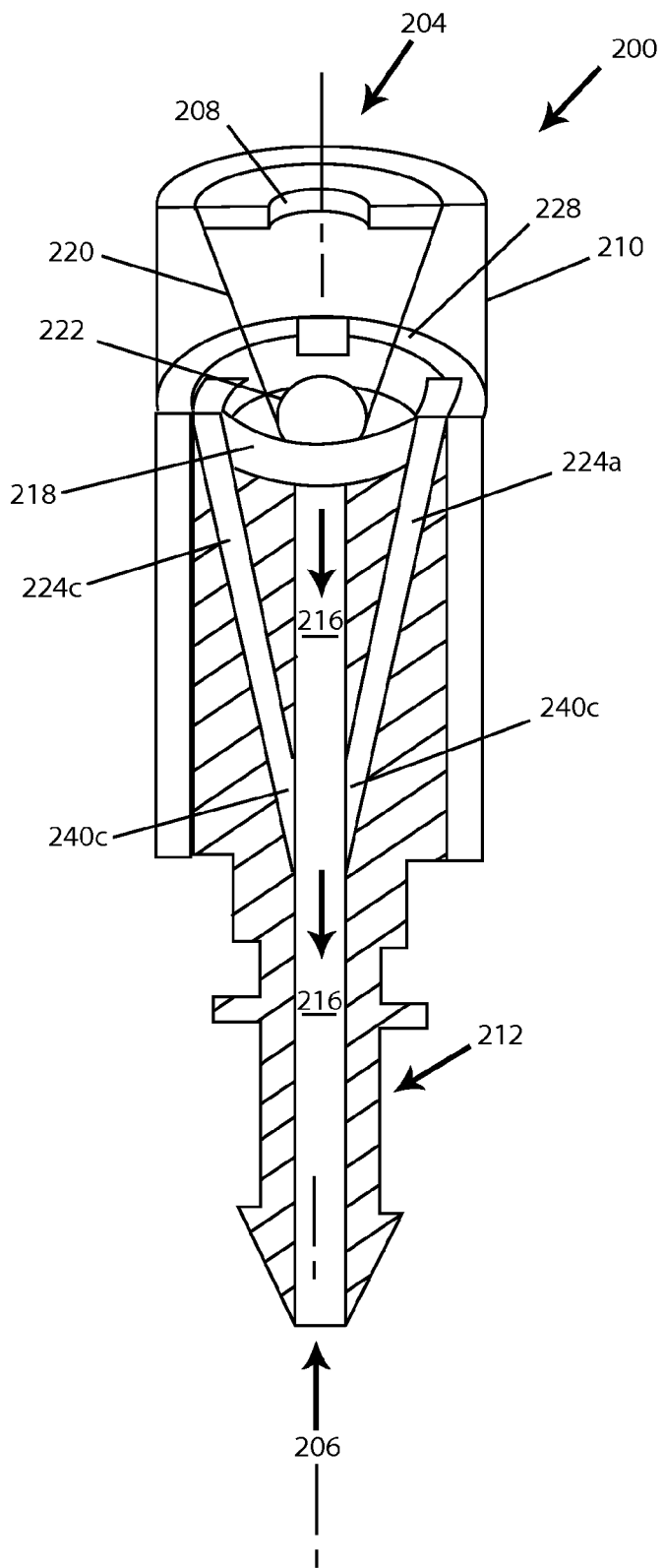
FIG. 6 is a cross-sectional isometric view of another example of an anti-siphon device.
Figure 7A:
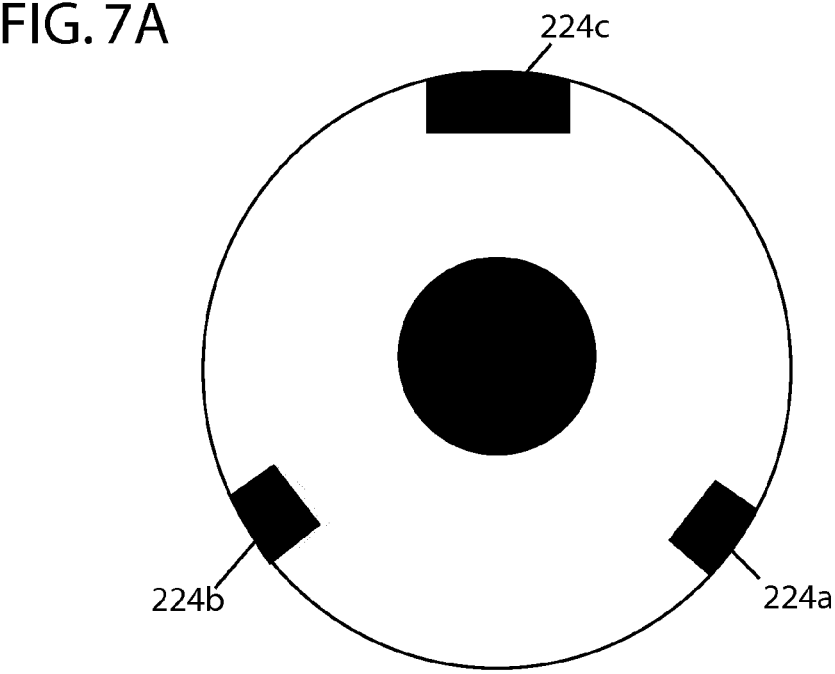
FIGS. 7A and 7B are a top section view of the anti-siphon device illustrating another example of a regulator.
Figure 7B:
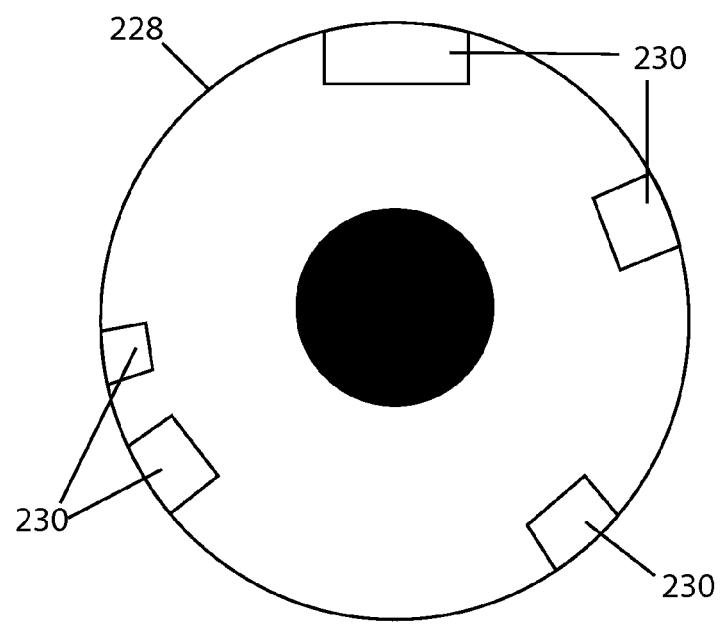

FIGS. 6-7B illustrate another example of an adjustable resistance, gravitationally activated, anti-siphon device 200. The anti-siphon device 200 can have three secondary flow paths 224a-c. Similar elements to the above example will be similarly referenced herein. The anti-siphon device 200 has an inlet 204 in aperture 208 form disposed in a housing 210 and an outlet 206 within a connector 212. Through a midline 214 of the housing 210 is a primary flow path 216. The primary flow path 216 connects the inlet port 204 to the outlet port 206 and is the main fluid path for the CSF. The primary flow path 216 can have a valve seat 218 disposed therein. Leading to the valve seat 218 is a sloped section 220 that can angle from the inlet port 204 to the valve seat 218, where the narrowest section is at the valve seat 218. Within the sloped section 220 can be a valve element 222, which in one example can be a ball.

When the housing 210 is upright position the ball 222 can be disposed in the seat 218 and the primary flow path 216 is sealed. FIG. 6 also illustrates a cross-section of two of the three secondary flow paths 224a, 224b, 224c. In this example, the secondary flow paths 224a, 224b, 224c are straight and have openings 226a, 226b, 226c near the inlet 204 and flow into the primary flow path 216 at a point below the valve seat 218 through orifices 240a, 240b, 240c.

FIG. 7A illustrates the openings 226a, 226b, 226c of the three secondary flow paths 224a, 224b, 224c. In this example, each flow path has a different flow characteristic. The first secondary flow path 224a ("F1") has the lowest flow rate, based on any of the factors mentioned above. The second secondary flow path 224b ("F2") has the next lowest flow rate, but greater than F1. The third secondary flow path 224c ("F3") has the largest flow rate of the secondary flow paths 224, but still a lower flow rate than the primary flow path 216 ("P1"). In relationship form: F1<F2<F3<P1

FIG. 7B illustrates a secondary flow path regulator 228 to control the flow of fluid into the secondary flow paths 224 by partially or fully blocking the openings 226. In this example, the regulator 228 has five to seven apertures 230. The apertures 230 are spaced to allow any combination of secondary flow paths 224 to be set. Each individual secondary flow path

224a, 224b, 224c can be selected as well as combinations of secondary flow paths 224a, 224b, 224c. FIG. 8 illustrates an example of the eight different configurations three secondary flow paths of varying flow resistance can supply. The dark sections represent the apertures 230. In this example the hydraulic capacity can be:

$$F1<F2<F1+F2<F3<F1+F3<F2+F3<F1+F2+F3<P1$$

In both hydraulic capacity examples F1 can have a value that 0<F1.

A user selected flow configuration can reduce the number of anti-siphon devices kept in stock. Currently, the devices are preset from the factory with a particular secondary flow rate, and thus the above example of the present invention can replace up to eight prior art devices. Here, the user can preset the secondary flow rate on the current invention and then change his mind, and change the settings again and again.

A further example is a method to form the anti-siphon valve discussed above. The method can include forming the primary flow path with the valve seat and disposing the valve element in the sloped section. Next, the secondary flow path can be formed and the regulator can be disposed over the secondary flow path to selectively occlude the secondary flow path.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

We claim:

1. An anti-siphon drainage device, comprising:
a housing forming an internal chamber;
an inlet port and an outlet port communicating with the internal chamber and fluidly connected by a primary flow path;
a valve seat associated with the primary flow path;
a sloped section extending from the valve seat inside the internal chamber;
a valve element disposed in the sloped section and capable of seating in the valve seat to restrict a fluid flow into the primary flow path from the inlet port;
a secondary flow path comprising an opening disposed approximate to the inlet port and an orifice disposed approximate to the outlet port;
a second secondary flow path separate from the secondary flow path and comprising a second opening; and
a regulator comprising an aperture to selectively open and close the opening of the secondary flow path and a second aperture to selectively open and close the second opening of the second secondary flow path in at least one of the following configurations: each of the openings individually opened,
wherein when the valve element is disposed in the valve seat and restricting the fluid flow into the primary flow path, the fluid flows into the secondary flow path.

2. The anti-siphon drainage device of claim 1, wherein when the inlet port is disposed approximately above the outlet port in a vertical direction, the valve element is disposed in the valve seat and restricting the fluid flow to the primary flow path, and
wherein when the inlet port is disposed approximately parallel the outlet port in a horizontal direction, the valve seat allows the fluid flow into the primary flow path.

3. The anti-siphon drainage device of claim 1, wherein at least one of the valve element and the valve seat allow a restricted fluid flow into the primary flow path when seated.

4. The anti-siphon drainage device of claim 1, wherein the primary flow path is hydraulically larger than the secondary flow path.

5. The anti-siphon drainage device of claim 1, wherein the secondary flow path is spiraled around the primary flow path.

6. The anti-siphon drainage device of claim 5, further comprising a second secondary flow path separate from the secondary flow path and comprising a second opening,
wherein the secondary flow path and the second secondary flow path are spiraled around the primary flow path as a double threaded screw, and
wherein the regulator further comprises a plurality of second apertures, which along with the aperture, are configured to selectively open and close the opening and the second opening.

7. The anti-siphon drainage device of claim 1, further comprising:
a third secondary flow path separate from both the secondary flow path and the second secondary flow path, and comprising a third opening,
wherein the regulator further comprises a third apertures, which along with the aperture and the second aperture, is configured to selectively open and close the third opening.

8. The anti-siphon drainage device of claim 7, wherein the regulator can selectively open and close the opening, the second opening, and the third opening in at least one of the following configurations: all open, all closed, each of the openings individually opened, and pairs of openings opened.

9. The anti-siphon drainage device of claim 8, wherein the primary flow path has a primary hydraulic capacity (P1), the secondary flow path has a secondary hydraulic capacity (F1), the second secondary flow path has a third hydraulic capacity (F2), and the third secondary flow path has a fourth hydraulic capacity (F3), and
further comprising a hydraulic relationship comprising: $F1<F2<F3<P1$.

10. The anti-siphon drainage device of claim 9, wherein the hydraulic relationship comprises: $F1<F2<F1+F2<F3<F1+F3<F2+F3<F1+F2+F3<P1$.

11. The anti-siphon drainage device of claim 1, wherein the disposition of the valve element in the valve seat is controlled by gravity.

12. A method of forming an anti-siphon drainage device, having a housing forming an internal chamber; an inlet port and an outlet port communicating with the internal chamber and fluidly connected by a primary flow path; a valve seat associated with the primary flow path; a sloped section extending from the valve seat inside the internal chamber; a valve element disposed in the sloped section and capable of seating in the valve seat to restrict a fluid flow into the primary flow path from the inlet port; a secondary flow path; a second secondary flow path separate from the secondary flow path; and a regulator, wherein when the valve element is disposed in the valve seat and restricting the fluid flow into the primary flow path, the fluid flows into the secondary flow path, comprising the steps of:
forming the primary flow path with the valve seat;
disposing the valve element in the sloped section;
forming the secondary flow path;
forming the second secondary flow path; and
disposing the regulator over the secondary flow path to selectively occlude the secondary flow path and the second secondary flow path in at least one of the following configurations: each of the openings individually opened.

13. The method of claim 12, wherein the method of forming the secondary flow path comprises spiraling the secondary flow path around the primary flow path.

14. The method of claim 12, further comprising the steps of:
forming the primary flow path with a first hydraulic characteristic; and
forming the secondary flow path with a second hydraulic characteristic,
wherein the first hydraulic characteristic is greater than the second hydraulic characteristic.

15. An anti-siphon drainage device, comprising:
a housing forming an internal chamber;
an inlet port and an outlet port communicating with the internal chamber and fluidly connected by a primary flow path;
a valve seat associated with the primary flow path;
a sloped section extending from the valve seat inside the internal chamber;
a valve element disposed in the sloped section and capable of seating in the valve seat to restrict a fluid flow into the primary flow path from the inlet port;
a secondary flow path comprising an opening disposed approximate to the inlet port and an orifice disposed approximate to the outlet port; and
a regulator comprising an aperture to selectively open and close the opening of the secondary flow path,
wherein when the valve element is disposed in the valve seat and restricting the fluid flow into the primary flow path, the fluid flows into the secondary flow path, and
wherein the regulator can restrict flow to the secondary flow path while fluid flows into the primary flow path.

16. The anti-siphon drainage device of claim 15, further comprising:
a second secondary flow path separate from the secondary flow path and comprising a second opening; and
a third secondary flow path separate from both the secondary flow path and the second secondary flow path, and comprising a third opening,
wherein the regulator further comprises a plurality of second apertures, which along with the aperture, are configured to selectively open and close the opening, the second opening, and the third opening.

17. The anti-siphon drainage device of claim 16, wherein the regulator can selectively open and close the opening, the second opening, and the third opening in at least one of the following configurations: all open, all closed, each of the openings individually opened, and pairs of openings opened.

18. A method of forming an anti-siphon drainage device, having a housing forming an internal chamber; an inlet port and an outlet port communicating with the internal chamber and fluidly connected by a primary flow path; a valve seat associated with the primary flow path; a sloped section extending from the valve seat inside the internal chamber; a valve element disposed in the sloped section and capable of seating in the valve seat to restrict a fluid flow into the primary flow path from the inlet port; a secondary flow path; and a regulator, wherein when the valve element is disposed in the valve seat and restricting the fluid flow into the primary flow path, the fluid flows into the secondary flow path, comprising the steps of:
forming the primary flow path with the valve seat;
disposing the valve element in the sloped section;
forming the secondary flow path;
disposing the regulator over the secondary flow path to selectively occlude the secondary flow path; and
selectively restricting the fluid flow to the secondary flow path while permitting the fluid flow to the primary flow path.

19. The method of claim 18, wherein the method of forming the secondary flow path comprises spiraling the secondary flow path around the primary flow path.

20. The method of claim 18, further comprising the steps of:
forming the primary flow path with a first hydraulic characteristic; and
forming the secondary flow path with a second hydraulic characteristic,
wherein the first hydraulic characteristic is greater than the second hydraulic characteristic.

* * * * *